United States Patent [19]

Labat et al.

[11] Patent Number: 4,827,040

[45] Date of Patent: May 2, 1989

[54] PROCESS OF DEGRADATION OF ALKYL POLYSULPHIDES INTO POLYSULPHIDES HAVING A LOWER SULPHUR CONTENT

[75] Inventors: Yves Labat, Pau; Guy Desgrandchamps, Billere, both of France

[73] Assignee: Societe Nationale Elf Aquitaine (Production), France

[21] Appl. No.: 843,087

[22] Filed: Mar. 24, 1986

[30] Foreign Application Priority Data

Mar. 25, 1985 [FR] France ................................. 85 04393

[51] Int. Cl.[4] ............................................ C07C 149/12
[52] U.S. Cl. ...................................... 568/21; 166/267; 166/902; 568/26
[58] Field of Search ..................... 568/21, 26; 166/902, 166/267, 310, 371

[56] References Cited

U.S. PATENT DOCUMENTS

| | | | |
|---|---|---|---|
| 2,435,732 | 2/1948 | Ayers et al. | 423/89 |
| 3,331,657 | 7/1967 | Peter et al. | 23/3 |
| 3,474,028 | 10/1969 | Bulian et al. | 208/230 |
| 3,545,916 | 12/1970 | Deicher et al. | 23/2 |
| 3,846,311 | 11/1974 | Sharp et al. | 252/8.55 B |
| 4,033,410 | 7/1977 | Kauffman | 166/902 |
| 4,239,630 | 12/1980 | Atkinson et al. | 252/8.55 B |
| 4,379,490 | 4/1983 | Sharp | 166/304 |
| 4,656,266 | 4/1987 | Bergorni et al. | 544/85 |
| 4,663,455 | 5/1987 | Bergorni et al. | 544/85 |

OTHER PUBLICATIONS

E. Blake, J. Am. Chem. Soc., 65, 1267–1269 (1943).
Houben–Weyl, Methoden der Organische Chemie, vol. XI/2 (1958), 747–748.
S. O. Jones et al., J., Amer. Chem. Soc., vol. 60, pp. 2452–2455, Oct. 1938.
E. Reid, Organic Chemistry of Bivalent Sulfur, vol. III, pp. 391–392 (1960), Chemical Publishing Co., Inc., N.Y.

Primary Examiner—Mary E. Ceperley
Attorney, Agent, or Firm—Ostrolenk, Faber, Gerb & Soffen

[57] ABSTRACT

The polysulphide is heated with a substance capable of dissolving elemental sulphur. After cooling, the polysulphide reduced to a lower numbver of S atoms is separated from the substance, which can be recovered.

An important use consists in converting the polysulphide to the form of dimethyl disulphide, the solvent used for the dissolution of sulphur deposited in conduits, particularly those used for natural gas.

8 Claims, No Drawings

PROCESS OF DEGRADATION OF ALKYL POLYSULPHIDES INTO POLYSULPHIDES HAVING A LOWER SULPHUR CONTENT

The invention relates to a process for the degradation of dialkyl polysulphides into their homologues having a lower sulphur content. In other words, the process according to the invention consists in reducing a dialkyl polysulphide so as to decrease the number of S atoms in its molecule. The invention also comprises the use of this process for the dissolution of sulphur deposited on the walls of conduits serving for the conveyance of gas containing this element; it is particularly useful in the exploitation of hypersulphided natural gas wells. The invention thus includes regeneration of the solvent used for the dissolution of sulphur deposited or capable of depositing upon the walls.

In certain industrial operations, the formation of dialkyl polysulphides of a sulphur content which can substantially exceed 2, particularly 3 to 8, is assisted, although there is a need for the disulphide. This is the case for example in a known process for the elimination of deposits of sulphur in natural gas conduits, where dimethyl disulphide is employed for the dissolution of the deposited sulphur. Such a process is described in U.S. Pat. Nos. 3846311 and 4239630. According to these disclosures, in the presence of an amine, dimethyl disulphide has a very considerable solvent power vis à vis elemental sulphur. The solubility of sulphur is not only of a physical nature but also because of the presence of a catalyst and because of the elevated temperature at which the dissolution occurs in wells and natural gas production pipelines, of a chemical nature in major part. In effect, the formation of dimethyl polysulphides, $R-S_x-R$, takes place, x varying from 3 to 8.

It is thus necessary to regenerate the solvent in order to be able to recycle it. A simple thermal treatment only allows regeneration of the part of the solvent corresponding to the physically dissolved sulphur. If it is desired to regenerate the major part of the initial solvent power, it is necessary to subject the solvent charged with sulphur to a chemical regeneration. The corresponding process forms part of the present invention which allows polysulphides to be converted into the disulphide form or at least to compounds similar to them, thus allowing reutilization of all of the initial solvent.

The new process according to the invention is characterised in that one or several dialkyl polysulphides are heated with a substance capable of dissolving elemental S and after cooling, this substance is then separated from the reduced polysulphide.

The first phase of the process can be shown diagrammatically in the following manner:

$$R-S_x-R + M \rightarrow R-S_2-R + MS_{(x-2)} \quad (1)$$

M designating the substance capable of combining with free sulphur which generally, as is known, has the form of $S_8$.

The invention results from the discovery that the reaction (1) can be carried out with any substance M capable of combining with free sulphur, provided the temperature is sufficiently elevated, in general being from 20° to 150° C. and preferably from 30° to 100° C. This substance M should be maintained in contact with the polysulphide or polysulphides for a sufficiently long period to degrade the polysulphide into the disulphide; this time naturally depends upon the nature of the substance M and the temperature, but it is generally of the order of 0.1 to 6 h; in industrial operations, it is of interest to operate at such a temperature that the degradation is terminated after about 0.1 to 3 h.

Substances capable of dissolving elemental sulphur are known in the art; they are in particular alkali metal, alkaline earth and ammoniacal bases, hydrosulphides, alkali metal sulphites as well as amines etc., as indicated for example in U.S. Pat. Nos. 3331657, 3489677, 3545916 or 4033410. Since in dialkyl polysulphides sulphides the bond between the sulphur atoms and the remainder of the molecule is quite strong, it is unexpected that compounds such as caustic soda, ammonia, amines and their thio-derivatives would be capable of detaching S atoms from polysulphide structures; however it has been clearly confirmed that this phenomenon according to reaction (1) occurs provided the temperature is sufficiently elevated.

Certainly, among numerous substances M which can be employed according to the invention, there are included compounds such as caustic soda, caustic potash, lime, ammonia, sulphides, sulphites and the hydrosulphides of sodium, potassium, calcium, NH$_4$ or various amines. Also, alkali metal mercaptides are suitable. Ammoniacal compounds and amines are the preferred substances M. By way of non-limitative example, reference can be made to amines such as ethylamine, propylamine, ethylenediamine, diethylamine, triethylamine, dipropylamine, butylamines, propylenediamine, pyridine, pyrroline, piperidine etc.

One of the advantages of amines and ammoniacal compounds is that these reactants can be regenerated after use for further use. In effect, the complex $MS_{(x-2)}$ formed during heating of M with the polysulphide can be dissociated by heating in order to liberate the S on the one hand and the amine or ammoniacal compound on the other, according to the reaction:

$$RNH_3^+ S_xH^- \rightarrow RNH_2 + [(x-1)/8]S_8$$

R being H or an alkyl corresponding to an amine, in particular one of those mentioned above. In general, this recovery can be effected by heating to a temperature of the order of 100° to 150° C. depending on the nature of the components.

The invention is applicable to polysulphides of various alkyl groups, particularly C$_1$ to C$_{18}$ which can have very varied sulphur contents (x) and most frequently from 3 to 8. The most interesting use for cleaning natural gas conduits, mentioned above, in particular uses dimethyl disulphide, CH$_3$SSCH$_3$, which after persulphuration to form CH$_3$S$_x$CH$_3$ with x=5 to 7, is degraded by the process of the invention into the disulphide or at least to a polysulphide where x is located between 2 and 3. The latter can be advantageously refused for dissolution of sulphur.

Since the reaction (1) implies a certain stoichiometrical relationship between the substance M and the sulphur S$_x$ of the polysulphide treated, the weight proportions of the substances M employed according to the invention must conform to this reaction (1).

The invention is illustrated by the non-limitative Examples which follow.

EXAMPLE 1

Use of NaOH 80 g of polysulphides $CH_3S_xCH_3$ where the mean of x is 6.5, are introduced into a reactor equipped with an agitator and a thermostat; 120 g of a 35% aqueous solution of caustic soda are then added. Thus 1.05 mole NaOH is provided per 0.34 mole of polysulphide.

The combination is maintained at 80° C. with agitation for 1 hour. After cooling to the ambient temperature, the organic phase amounting to 30 g is decanted, the average composition of which is $CH_3S_{2.1}$—$CH_3$ (0.3 mole).

It can be seen that the caustic soda has eliminated 4.4 atoms of S while degrading the polysulphide to the form of a compound very close to dimethyl disulphide. Production of the latter is thus effected in a yield of 0.3 : 0.34 =0.88 or 88%.

EXAMPLE 2

Use of a mercaptide

The mode of operation is the same as in Example 1, but the caustic soda is replaced by an aqueous solution of sodium methyl thiolate $CH_3SNa$; this solution was obtained by the absorption of methyl mercaptan in a 35% caustic soda solution. For the same quantity of 80 g $CH_3S_{6.5}CH_3$, or 0.34 mole, 0.6 mole of $CH_3SNa$ is used.

After heating and decantation, 50 g of the organic phase of an average composition $CH_3S_{2.12}CH_3$, or 0.51 mole is obtained. As in the foregoing Example, the polysulphide has been converted into a composition very close to dimethyl disulphide; the production yield of the latter is $$0.51 : \left(0.34 + \frac{0.60}{2}\right) = 0.797 \text{ or } 79.7\%.$$

The treatment of sodium methyl thiolate has the advantage of producing dimethyl disulphide in the reaction conditions; it can thus constitute a means for exploiting use of the solvent for use of the mercaptide which leads to the formation of fresh dimethyl disulphide, while degrading the polysulphide.

EXAMPLE 3

Use of sodium sulphite 80 g or 0.34 mole of the same mixture of polysulphides having x =6.5, as in the foregoing Examples is reacted with 274 g of a 35% aqueous solution of $Na_2SO_3$ (0.76 mole) at 80° C. for 2 hours. After cooling to the ambient temperature and decantation, 46 g of the polysulphide $CH_3S_{3.3}CH_3$ or 0.34 mole, are obtained.

It can be seen that the yield of the latter reduced polysulphide amounts to 100% with respect to the initial polysulphide. While in this operation the degradation of x only goes from 6.5 to 3.3, it is possible to take it further, by employing more sulphite, particularly 1 mole.

EXAMPLE 4

Use of ammonium sulphide

Using the conditions of Example 1, a mixture of 80 g of the same polysulphides having x =6.5, or 0.34 mole, with an aqueous solution of 0.3 mole of ammonium sulphide are reacted. This solution has been obtained by the action of $H_2S$ on an ammoniacal solution.

After the reaction, cooling and decantation, the organic phase comprising 42 g is constituted by $CH_3S_{3.5}CH_3$ (0.295 mole).

The yield of polysulphide degraded to $S_{3.5}$ amounts to 0.295 : 0.34=0.867, or 86.7%.

Degradation to about $S_2$ can be effected by employing about 0.45 mole of $(NH_4)_2S$ per 0.34 mole of the initial polysulphide.

EXAMPLE 5

Use of ammonium sulphide at a more elevated temperature.

Example 4 is repeated, but the temperature is 110° C. and the duration of the reaction is 1 hour. 33 g of an average composition $CH_3S_{2.7}CH_3$ or 0.28 mole, is obtained.

The yield of production of this product is 0.28 0.34=82%.

It can be seen that by suitably regulating the proportion of the reactants, the temperature and the duration of heating, the polysulphide can be degraded to any desired degree.

EXAMPLE 6

Use of ethylamine 80 g of dimethyl polysulphide $CH_3S_{6.5}CH_3$, or 0.34 mole, is reacted with 100 ml of an aqueous solution of 0.5 mole of ethylamine, at 70° C. in a closed reactor with agitation for 3 h.

After cooling and decantation, 36 g of dimethyl polysulphide, $CH_3S_{3.5}CH_3$ (0.25 mole) is recovered. This corresponds to a yield of 0.25 : 0.34 32 75%.

The degradation can be taken further to about $S_2$ with 0.7 mole of ethylamine during 4 hours.

The amine is recovered by heating the residue separated from the polysulphide at a temperature of 120° to 150° C.

EXAMPLE 7

Use of ethylene diamine

The operations of Example 6 are repeated with ethylene diamine in place of ethylamine. The degraded product corresponds to the average composition $CH_3S_{2.2}CH_3$.

EXAMPLE 8

Regeneration of a polysulphide which has physically dissolved sulphur 3.2 g of sulphur (0.1 mole) is dissolved in 100 g of dimethyl polysulphide $CH_3$—$S_{6.5}$—$CH_3$ (or 0.43 mole). The solution obtained is reacted with 250 ml of an aqueous solution of ammonium sulphide, prepared by the introduction of $H_2S$ into 250 ml of a 2N ammoniacal solution. After reaction at 80° C. with agitation for 1 hour, cooling and decantation, 42 g of an organic phase is recovered comprising $CH_3$—$S_{2.5}$—$CH_3$ (0.38 mole). This organic phase no longer contains physically dissolved sulphur.

The yield of polysulphide degraded to $S_{2.5}$ amounts to 0.38 : 0.43=0.88 or 88%.

EXAMPLE 9

Cyclic re-use of regenerated polysulphide 3,000 g of fresh dimethyl disulphide with 2,000 g of elemental sulphur are introduced into a stainless steel reactor and the contents are heated with agitation at 80° C. for 2 hours. Then 2300 g of an aqueous solution of ammonium sulphide containing 15.7 moles of $(NH_4)_2S$, prepared by the reaction of a stream of $H_2S$ on an aqueous ammonium solution, are added. The mixture is then heated to 90° C. and agitated for 3 hours.

After settling and separation of the aqueous layer of $NH_4$ polysuphide formed, the organic layer of dimethyl polysulphide is recovered; the latter was reused for a new dissolution of sulphur operated as above. Then a third similar cycle was effected.

The following Table gives the results of these three successive dissolutions with recovery of the dissolved polysulphide.

TABLE

| Cycle No. | 1 | 2 | 3 |
|---|---|---|---|
| Reactants used: | | | |
| moles of $CH_3S_xCH_3$ | 32 | 27.9 | 27.5 |
| content x | 4 | 4.2 | 4 |
| gram-atoms of S | 62.6 | 27.8 | 26 |
| gr. mols. $(NH_4)_2S$ | 15.7 | 14 | 13 |
| total gram-atoms of S | 142.6 | 131 | 122 |
| Obtained: | | | |
| Aqueous solution: | | | |
| Gram-atoms of S | 44.1 | 42.5 | 38.1 |
| gr. mols. $(NH_3)$ | 21.7 | 20.3 | 18.8 |
| Organic solution: | | | |
| moles of $CH_3S_xCH_3$ | 27.9 | 27.5 | 26 |
| content x | 3.2 | 3.03 | 2.9 |
| total gram-atoms of S | 133.4 | 126 | 113.5 |
| Results: | | | |
| Rate of regeneration of solvent | 0.87 | 0.985 | 0.945 |
| Rate of recovery of sulphur | 0.935 | 0.96 | 0.86 |
| Rate of recovery of $NH_3$ | 0.69 | 0.725 | 0.73 |

Although effected without special precautions, these tests have given good results, as shown by the increased rates for recovery of solvent and sulphur (0.86 to 0.98); it is thus reasonable to expect excellent results after optimization on an industrial scale.

EXAMPLE 10

The organic phase obtained after the 3rd cycle of Example 9, i.e. 26 mols of $CH_3S_xCH_3$, x being 2.9, has been mixed with 1900 g of an aqueous solution containing 13 mols $(NH_4)_2S$. The mixture has then been heated at 90° C. during 3 hours under stirring, without adding sulfur. After standing, the separated organic phase was constituted of $CH_3S_xCH_3$ the x of which was 2.4.

Thus it is seen that an already degraded polysulfide may still be degraded without the addition of sulfur.

We claim:

1. A method of treating a dialkyl polysulphide of the formula $R—S_x—R$, where R is a 1 to 18 carbon atom alkyl and x is a number greater than 2 so as to lower the value of the number x in the polysulphide which comprises contacting said polysulphide with an aqueous solution of an agent selected from the group consisting of $C_{2-6}$ amine sulphide and ammonium sulphide at a temperature within the range of 20° to 150° C. for a time sufficient to lower the value of the number x and thereafter separating the resulting dialkyl polysulphide of lower x value from the aqueous solution.

2. Method according to claim 1, wherein said contacting is effected at a temperature of 50° C. to 110° C. for 1–3 hours.

3. Method according to claim 2 in which after dialkyl polysulphide of lower x value is separated from the aqueous solution, an amine or ammonia is generated by heating the aqueous solution at a temperature of 100° to 150° C.

4. Method according to claim 1 wherein R is methyl, the lower rank dimethyl polysulphide is contacted with sulphur so as to form dimethyl polysulphide whose sulphur rank x is 2.4 to 8 and said contacting and separation steps are repeated thereon.

5. Method according to claim 1 in which the number x in the dialkyl polysulphide to be treated is 3 to 8.

6. Method according to claim 1 in which the amine sulphide is selected from the group consisting of the sulphides of ethylamine, propylamine, ethylene diamine, diethylamine, triethylamine, dipropylamine, butylamine, propylene diamine, pyridine, pyrroline and piperidine.

7. Method according to claim 3 in which R is methyl and x in the dialkyl polysulphide to be treated is 3 to 8.

8. Method according to claim 1, wherein the aqueous solution contains by weight 20 to 60% of said agent.

* * * * *